United States Patent [19]
Mori et al.

[11] Patent Number: 5,667,644
[45] Date of Patent: Sep. 16, 1997

[54] METHOD FOR PRODUCING A DIMERIZED ALDEHYDE

[75] Inventors: Tomoyuki Mori; Kouichi Fujita; Yuuji Kajita; Masaki Takai, all of Kurashiki, Japan

[73] Assignee: Mitsubishi Chemical Corporation, Tokyo, Japan

[21] Appl. No.: 599,242

[22] Filed: Feb. 9, 1996

[30] Foreign Application Priority Data

Feb. 13, 1995 [JP] Japan ................... 7-024083
Sep. 11, 1995 [JP] Japan ................... 7-232491
Nov. 7, 1995 [JP] Japan ................... 7-288461

[51] Int. Cl.$^6$ .............................................. C07C 45/82
[52] U.S. Cl. ........................ 203/17; 203/29; 203/37; 203/38; 568/420
[58] Field of Search ................. 203/17, 28, 29, 203/37, 38; 568/420

[56] References Cited

U.S. PATENT DOCUMENTS 5,362,918  11/1994  Aizawa et al. ................... 568/594
5,420,341   5/1995  Argyropoulos et al. ........... 560/224

FOREIGN PATENT DOCUMENTS 2 058 532     5/1971  France .
WO 93/20034  10/1993  WIPO .

*Primary Examiner*—Cynthia L. Nessler
*Attorney, Agent, or Firm*—Oblon, Spivak, McClelland, Maier & Neustadt, P.C.

[57] ABSTRACT

A method for producing a dimerized aldehyde, which comprises subjecting a feed aldehyde to a condensation reaction and a dehydration reaction in the presence of a basic catalyst, wherein the feed aldehyde is the one having one or two hydrogen atoms at the α-position, an organic feed stream containing the feed aldehyde is supplied to a reactive distillation column, and the condensation reaction and the dehydration reaction are carried out simultaneously in the reactive distillation column.

29 Claims, 2 Drawing Sheets

METHOD FOR PRODUCING A DIMERIZED ALDEHYDE

BACKGROUND OF THE INVENTION

1. Field of the Invention

The present invention relates to a method for producing a dimerized aldehyde which comprises subjecting an aldehyde to a condensation reaction and a dehydration reaction in the presence of a basic catalyst. Particularly, it relates to a method for producing a dimerized aldehyde at a high selectivity by suppressing formation of undesirable high boiling point compounds such as a trimer of aldehyde in the condensation reaction and the dehydration reaction of an aldehyde.

2. Discussion of Background

Heretofore, a method for producing a dimerized aldehyde has been known in which an aldehyde is subjected to a condensation reaction (also known as "aldol condensation" or "aldolization") and a dehydration reaction using a basic compound such as an aqueous alkaline solution as a catalyst. For example, when n-butyraldehyde (hereinafter referred to as NBD) is subjected to a condensation and a dehydration reaction, 2-ethylhexenal (hereinafter referred to as EPA) is obtainable. However, it is known that in the conventional condensation and dehydration reaction method, the dimerized aldehyde (a kind of dimers) as the desired product is likely to further react to form high boiling point compounds such as a trimer, a tetramer, etc. Consequently, the yield of the dimerized aldehyde tended to be low. To solve such a problem, the following various improvements have heretofore been proposed.

For example, Japanese Examined Patent Publication No. 24787/1964 discloses a method wherein NBD solution and an aqueous alkaline solution are counter-currently contacted in a column packed with a packing material or perforated plates, and vibration is given to this column to disperse NBD solution and thereby to prepare EPA.

Japanese Examined Patent Publication No. 43810/1977 discloses a method wherein NBD solution and an aqueous alkaline solution are reacted at a temperature of from 120° to 130° C. under a pressure of from 4 to 5 kg/cm$^2$G using two reactors i.e. a stirred tank reactor and a tubular reactor.

Further, French Patent 2,058,532 discloses a method wherein acetaldehyde is subjected to aldolization with a dilute sodium hydroxide aqueous solution by means of a perforated plate tower. It is disclosed that in order to carry out the reaction at a desired selectivity, the aldolization is stopped at a desired stage by adding acetic acid to the bottom of the column to neutralize the alkali catalyst. In this method, if it is attempted to conduct a dehydration reaction at the same time as the aldolization reaction of acetaldehyde by an alkali catalyst, enolate ions tend to form due to transfer of hydrogen at the γ-position of croton aldehyde as a dimer, and the enolate ions are likely to repeat condensation to finally form a polymer. To prevent such a possibility, a kind of a reaction terminator, such as acetic acid, is introduced into the reaction system.

On the other hand, in an industrial operation of such a condensation and dehydration reaction, it is common that after separating from the reaction solution an oil layer containing a product such as EPA by such a method as oil-water separation, an aqueous layer being an aqueous alkaline solution, is recycled to the reactor for reuse. However, due to water formed by the dehydration reaction, the concentration of the alkali catalyst in the aqueous solution decreases. Further, as the volume of the aqueous alkaline solution increases, it is necessary to purge a part of the recycling aqueous alkaline solution depending upon the formed water. Accordingly, it has been necessary to supplement a basic catalyst afresh to the reactor to compensate the purged portion.

Further, the above-mentioned purged solution contains water polluting substances such as sodium hydroxide catalyst and sodium butyrate formed by a Cannizzaro reaction which partially takes place in the reactor. Accordingly, it is necessary to conduct treatment such as neutralization treatment to prevent pollution before discharging it as waste water, and a substantial investment for such an installation has been required.

However, by the method disclosed in Japanese Examined Patent Publication No. 24787/1964, the yield of formed EPA is at a level of 94% at best. Also in the method disclosed in Japanese Examined Patent Publication No. 43810/1977, large amounts of aldol products and high boiling point compounds will form, and unreacted NBD will be substantial at a level of a few %. Thus, in the prior art, a dimerized aldehyde such as EPA has not been obtained in satisfactory yield.

On the other hand, to solve such a problem, there has been proposed a method wherein high boiling point compounds formed as by-products, are decomposed into a feed aldehyde and an unsaturated aldehyde for recovery (Japanese Unexamined Patent Publications No. 24952/1964 and No. 17907/1964), or a method wherein before the aldol condensation product is introduced to the hydrogenation reaction step, high boiling compounds are separated therefrom in an evaporator, and the separated high boiling point compounds are recycled to the condensation reaction step, so as to improve the yield of the condensation step (Japanese Unexamined Patent Publication No. 41309/1976). However, if such a process is to be adopted on an industrial scale, the process steps will be complex, and a decomposition apparatus or a separating apparatus for high boiling point compounds will further be required. Accordingly, the installation cost will increase, such being economically disadvantageous.

Further, in the method disclosed in French Patent 2,058,532, acetic acid is added, whereby it is practically impossible to repeatedly reuse the alkaline catalyst. Therefore, such a method is commercially disadvantageous.

On the other hand, some proposals have been made to solve the water pollution problem.

For example, in Japanese Unexamined Patent Publication No. 28109/1978 by the present inventors, the reaction solution is subjected to oil-water separation, whereupon at least a part of the obtained aqueous phase is distilled, so that water corresponding to the amount of water formed by dehydration, is distilled off and discharged in the form which is free from a water polluting substance.

This method is an advanced method from the viewpoint of the environmental protection. However, in addition to the reactor, a distillation equipment is required, and thus a substantial investment for the installation is required. For this reason, this method is not satisfactory for an industrial application.

Further, Japanese PCT Publication No. 505390/1995 proposes a method in which the product stream from an aldolization-dehydration reaction using an aqueous alkali catalyst solution is introduced directly, without oil-water separation, to a distillation column for the next step, and from the top of the column, a heterogeneous azeotrope of water and aldehyde, is recovered and subjected to oil-water separation, so that waste water can be discharged in a form which requires no neutralization treatment.

However, like the above-mentioned Japanese Unexamined Patent Publication No. 28109/1978, the method of Japanese PCT Publication No. 505390/1995 requires an extra distillation column and thus an extra cost for the installation. Further, the aldehyde in the azeotrope distilled from the top of the column in this method is unreacted aldehyde as the feed material for the condensation reaction and has a large solubility to water. Accordingly, an extra post-treatment step for recovering the unreacted aldehyde dissolved in the aqueous layer is required at the time of removing formed water by the oil-water separation, thus leading to a complication of the process. Thus, this method was not satisfactory for an industrial application.

SUMMARY OF THE INVENTION

The present invention has been made in view of the above circumstances, and it is an object of the present invention to provide a method for producing an unsaturated dimerized aldehyde by a condensation and dehydration reaction of an aldehyde, whereby the dimerized aldehyde can be produced in good yield by minimizing formation of high boiling point compounds without requiring complicated treatment steps which are economically disadvantageous.

The present inventors have conducted extensive studies to accomplish the above objects and as a result, have found that in a method wherein an aldehyde having one or two hydrogen atoms at the α-position is subjected to a condensation reaction and a dehydration reaction with a basic catalyst, it is possible to suppress formation of high boiling point compounds and to obtain a dimerized aldehyde in good yield, by simultaneously carrying out the condensation reaction and the dehydration reaction in a reactive distillation column.

In a first aspect, the present invention provides a method for producing a dimerized aldehyde, which comprises subjecting a feed aldehyde to a condensation reaction and a dehydration reaction in the presence of a basic catalyst, wherein the feed aldehyde is the one having one or two hydrogen atoms at the α-position, an organic feed stream containing the feed aldehyde is supplied to a reactive distillation column, and the condensation reaction and the dehydration reaction are carried out simultaneously in the reactive distillation column.

In a second aspect, the present invention provides a method for producing a dimerized aldehyde, which comprises subjecting a feed aldehyde to a condensation reaction and a dehydration reaction in the presence of a basic catalyst, wherein an organic feed stream containing the feed aldehyde is supplied to a reactor, and the condensation reaction and the dehydration reaction are carried out simultaneously in the reactor, wherein contact of the feed aldehyde with the basic catalyst in the reactor is carried out in such a manner that the feed aldehyde in a gas-liquid mixed state is intimately contacted with the basic catalyst in a liquid state.

Further, in a third aspect, the present invention provides a method for producing a dimerized aldehyde, wherein a distillation column is used which has a feed inlet at an intermediate section of the column and which is provided with liquid phase-maintaining means located in the column above and below the feed-inlet, wherein an alkali catalyst is present in the liquid phase-maintaining means located below the feed inlet, a feed aldehyde containing an aldehyde having two hydrogen atoms at the α-position, is supplied from the feed inlet, a condensation reaction and a dehydration reaction of the feed aldehyde are carried out in the column to form a dimerized aldehyde having an unsaturated bond, a low boiling point fraction containing the feed aldehyde and water is distilled from above the feed inlet of the distillation column, while a formed mixture containing the dimerized aldehyde is withdrawn from below the feed inlet of the distillation column, and the dimerized aldehyde is recovered from the formed mixture.

DETAILED DESCRIPTION OF THE PREFERRED EMBODIMENTS

Figure 1:
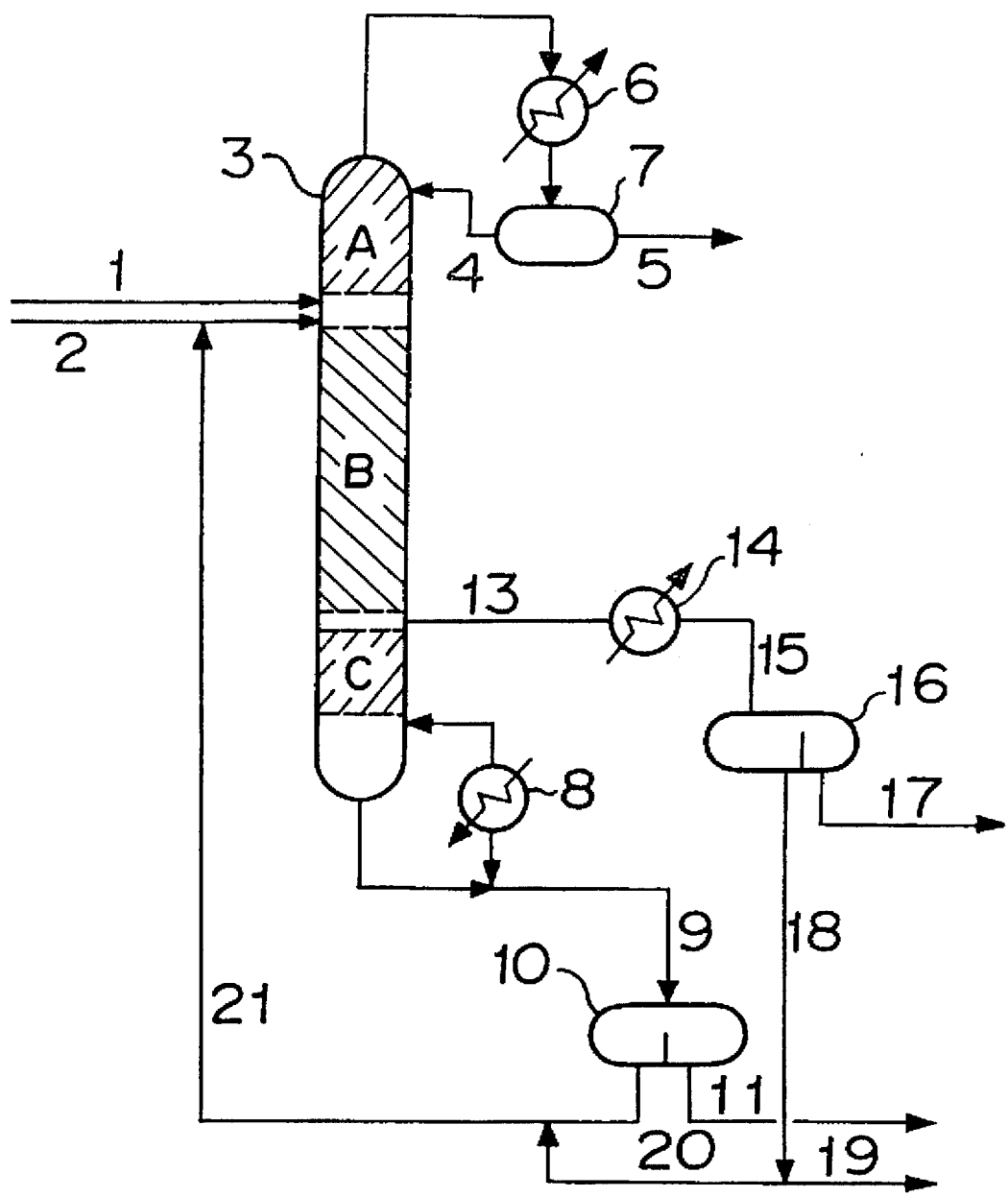
FIG. 1 is a view illustrating the flow diagram of the reaction apparatus used in Examples 1 to 6.

Now, the present invention will be described in detail.

The feed aldehyde to be used in the present invention, is an aldehyde having 1 or 2 hydrogen atoms at the α-position. Particularly preferred is a saturated aldehyde having two hydrogen atoms at the α-position. The feed aldehyde may be a single substance or a mixture of a plurality of aldehydes. Specifically, n-butyraldehyde, isobutyraldehyde, valeraldehyde or 2-methylbutyradehyde may, for example, be mentioned. Preferred is n-butyraldehyde or valeraldehyde. Among them, it is particularly preferred to employ n-butyraldehyde.

The present invention is a method wherein the condensation reaction and the dehydration reaction are simultaneously carried out in a reactive distillation column. Accordingly, it is preferred that the aldehyde having two hydrogen atoms at the α-position, is contained at least 50 wt %, more preferably at least 70 wt %, particularly preferably at least 90 wt %, of the organic feed stream containing the feed aldehyde to be supplied to the reactive distillation column, from the viewpoint that the effects of the present invention can adequately be accomplished in an industrial operation. Here, when the content of the aldehyde having two hydrogen atoms at the α-position, is calculated, in a case where the above-mentioned organic feed stream to be supplied to the reactive distillation column contains a basic catalyst or its aqueous solution, the calculation is made on the basis of the weight of the organic component excluding the catalyst or its aqueous solution.

Further, in the present invention, water formed by the dehydration reaction is withdrawn in a vapor state from the reactive distillation column where the condensation reaction and the dehydration reaction are carried out simultaneously, whereby it is possible to discharge waste water in such a state where it does not substantially contain the basic catalyst and a water-polluting substance such as sodium carboxylate which forms in a small amount by the reactions.

Further, in order to minimize the loss of the feed aldehyde, the position in the reactive distillation column from which the formed water is withdrawn, is preferably a position where the weight ratio of the dimerized aldehyde to the feed aldehyde in the vapor composition (hereinafter referred to as a DA/UA value) is at least 0.5. More preferably, the DA/UA value is at least 0.8, and most preferably, the DA/UA value is at least 0.9.

In another method for discharging the water formed by the dehydration reaction, a basic catalyst liquid stream or a mixed liquid stream of the basic catalyst liquid and the reaction product, is withdrawn from the reactive distillation column in which the condensation reaction and the dehydration reaction are simultaneously carried out, and a part of this liquid stream is subjected to flushing to drive off the formed water, whereby the formed water can be discharged in a state where it does not substantially contain the basic catalyst and a water-polluting substance such as sodium butyrate which forms in a small amount by the reactions, in the same manner as the above-mentioned method.

In a case where the liquid stream withdrawn from the reactive distillation column is in the form of an emulsion, a part thereof may be flushed in the form of the emulsion, or before flushing, it may be subjected to oil-water separation, and a part of the aqueous layer containing the basic catalyst liquid, thus separated, is flushed.

In order to minimize the loss of the feed aldehyde, the position in the reactive distillation column from which the basic catalyst liquid stream or the mixed liquid stream of the basic catalyst and the reaction product, is withdrawn, is preferably a position where the weight ratio of the dimerized aldehyde to the feed aldehyde in the liquid composition (hereinafter referred to as LDA/LUA value) is at least 0.5, more preferably a position where the LDA/LUA value is at least 0.8, most preferably a position where the LDA/LUA is at least 0.9.

The basic catalyst to be used in the present invention is not particularly limited so long as it is capable of promoting the condensation reaction and the dehydration reaction. For example, water soluble basic compounds may be used including basic compounds containing an alkali metal, such as sodium hydroxide, potassium hydroxide, sodium oxide, potassium oxide, sodium methoxide and potassium ethoxide, various amine compounds such as trimethylamine, triethylamine, tripropylamine, diethylamine, dipropylamine and dibutylamine, and quaternary ammonium hydroxide compounds such as trimethylbenzylammonium hydroxide, tetramethylammonium hydroxide and tetraethylammonium hydroxide. Such a basic catalyst is used usually preferably in the form of a solution employing a suitable solvent. In such a case, the solvent for the basic catalyst is not particularly limited so long as it is capable of dissolving the catalyst. For example, water, an alcohol or a mixed solution thereof may be employed.

When this method is conducted on an industrial scale, a water insoluble or hardly soluble basic solid catalyst may also be used from the viewpoint that separation of the catalyst from the reaction product and recycling of the catalyst can be facilitated. Such a water-insoluble or hardly soluble basic solid catalyst may, for example, be an alkaline earth metal-containing basic compound such as magnesium hydroxide, calcium hydroxide, strontium hydroxide, barium hydroxide, magnesium oxide, calcium oxide, strontium oxide or barium oxide, or a catalyst having such an alkaline earth metal-containing basic compound supported on a carrier by a conventional method, or a basic ion exchange resin.

Among such basic catalysts, preferred is an aqueous solution of an inorganic basic compound, particularly an aqueous solution of e.g. sodium hydroxide, potassium hydroxide or lithium hydroxide, from the viewpoint of the separability from the feed material and the reaction product.

The concentration of the basic catalyst is usually preferably from 0.5 to 10 wt %.

The second feature of the present invention is that in the method for producing a dimerized aldehyde by subjecting a feed aldehyde to a condensation reaction and a dehydration reaction simultaneously in a reactor in the presence of a basic catalyst, the feed aldehyde and the basic catalyst are contacted in a certain specific state in the reactor, whereby the dimerized aldehyde can be produced in good yield and highly selectively.

Specifically, the feed aldehyde and the basic catalyst liquid are introduced into a reactor such as a reactive distillation column, and the feed aldehyde in a gas-liquid mixed state is intimately contacted with the basic catalyst in a liquid state to conduct the condensation reaction and the dehydration reaction simultaneously, whereby the dimerized aldehyde can be produced in good yield. This is a novel reaction system which is totally different from the conventional concept of the condensation reaction and the dehydration reaction of the feed aldehyde with a basic catalyst. Namely, the conventional reaction mechanism of the condensation and the dehydration reaction is solely composed of the reaction by liquid-liquid contact of the catalyst solution and the feed aldehyde i.e. solely by the mass transfer between a liquid and a liquid. Whereas according to the condensation and the dehydration reaction of the present invention, not only the conventional liquid-liquid mass transfer, but also the gas-liquid mass transfer from the gaseous feed aldehyde to the basic catalyst liquid proceeds at a level equal to or swifter than the liquid-liquid mass transfer.

The reaction temperature and pressure for the intimate contact of the basic catalyst liquid and the feed aldehyde, have to be selected so that the feed aldehyde can be maintained in a gas-liquid mixed state. For example, when the feed aldehyde is NBD, the contact temperature is usually from 50° to 180° C., preferably from 70° to 100° C., and the pressure is usually from 0.4 to 12.0 kg/cm$^2$A, preferably from 0.8 to 2.0 kg/cm$^2$A. If the contact reaction temperature is lower than 50° C., the reaction rate tends to be low, such being undesirable. On the other hand, if it exceeds 180° C., there will be a loss of the feed aldehyde by the heat, and consequently, the yield will be low.

The mode for supplying the feed aldehyde and the basic catalyst is not particularly limited. Usually, one or both of them are preferably continuously supplied. It is particularly preferred to supply the feed aldehyde continuously.

As a preferred embodiment of the present invention, it is possible to employ a method for producing a dimerized aldehyde, wherein a distillation column is used which has a feed inlet at an intermediate section of the column and which is provided with liquid phase-maintaining means located in the column above and below the feed inlet, wherein an alkali catalyst is present on the liquid phase-maintaining means located below the feed inlet, a feed aldehyde containing an aldehyde having two hydrogen atoms at the α-position, is supplied from the feed inlet, a condensation reaction and a dehydration reaction of the feed aldehyde are carried out in the column to form a dimerized aldehyde having an unsaturated bond, a low boiling point fraction containing the feed aldehyde and water is distilled from above the feed inlet of the distillation column, while a formed mixture containing the dimerized aldehyde is withdrawn from below the feed inlet of the distillation column, and the dimerized aldehyde is recovered from the formed mixture.

In this case, it is preferred to withdraw the formed mixture containing the dimerized aldehyde from an intermediate position between the feed inlet and the bottom of the distillation column. The liquid phase-maintaining means is preferably the one, at least a part of which consists of plates or a packing material. With a view to suppressing formation of high boiling point compounds, it is preferred to employ a liquid phase-maintaining means located below the feed inlet i.e. the one having theoretical plates of from 2 to 50 plates in the reaction zone.

In a case where a distillation column provided with a reboiler is used as the distillation column, if the liquid stream supplied to the reboiler contains a large amount of the reaction product relative to the basic catalyst liquid, decomposition of the reaction product and formation of high boiling substances tend to occur, whereby the yield will substantially decrease. Accordingly, the liquid stream to be supplied to the reboiler is preferably the one wherein the weight ratio of the organic phase composed mainly of the dimerized aldehyde to the aqueous phase containing the basic catalyst, is at most 0.1.

Now, one embodiment of the present invention will be described with reference to FIG. 1.

Referring to FIG. 1, the feed aldehyde and an aqueous solution of the basic catalyst are supplied from lines 1 and 2 of a reactive distillation column 3, respectively. In the reactive distillation column, the feed aldehyde and the basic catalyst will contact with each other, whereby a condensation reaction and a dehydration reaction will take place, and the reactive distillation is carried out so that a vapor ascending in the column heated by the reboiler 8 and a descending liquid will maintain substantially gas-liquid equilibrium.

The vapor distilled from the top of the column will be cooled and condensed by a condenser 6, and a part of unreacted feed aldehyde will be returned to an upper section of the reactive distillation column 3. Further, from a line 13, the formed dimerized aldehyde is withdrawn together with water in a vapor phase, whereupon the dimerized aldehyde is separated and recovered by oil-water separation. On the other hand, from the bottom of the column, the aqueous basic catalyst solution and high boiling point compounds are withdrawn and subjected to oil-water separation, whereupon the aqueous basic catalyst solution is recycled to the reactive distillation column.

Further, an embodiment for withdrawal of water formed by the reaction will be described with reference to FIG. 2.

Figure 2:
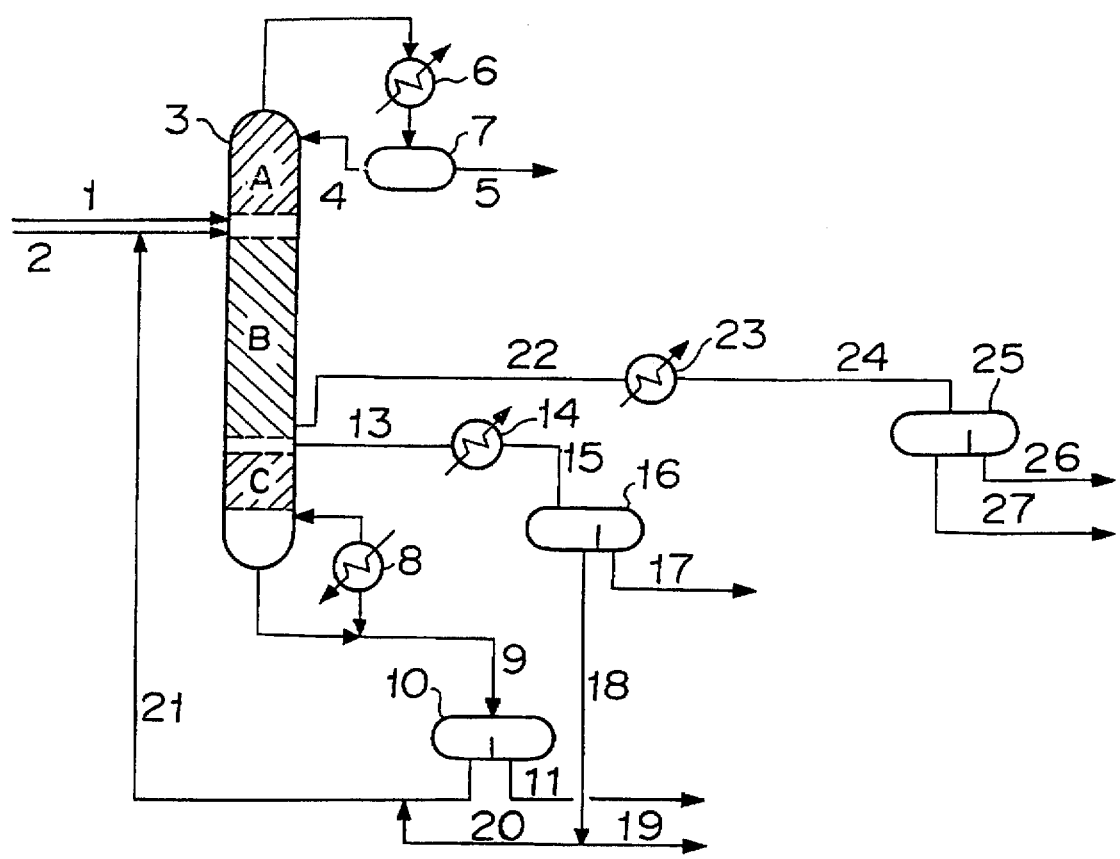
FIG. 2 is a view illustrating the flow diagram of the reaction apparatus used in Examples 7 to 10.

Referring to FIG. 2, the feed aldehyde and an aqueous solution of the basic catalyst are, respectively, supplied by lines 1 and 2 of a reactive distillation column 3. In the reactive distillation column 3, the feed aldehyde and the basic catalyst will contact with each other, whereby a condensation reaction and a dehydration reaction will take place, and the reactive distillation is carried out so that a vapor ascending in the column under heating by a reboiler 8 and a descending liquid will maintain substantially gas-liquid equilibrium.

The vapor distilled from the top of the tower is cooled and condensed by a condenser 6, whereupon the entire amount or the majority of unreacted feed aldehyde is returned by a line 4 to an upper section of the reactive distillation column 3. Further, low boiling point components formed in a very small amount will be withdrawn from a line 5, if necessary. Further, from a line 13, the dimerized aldehyde formed by the reaction is withdrawn in a liquid state, then cooled by a condenser 14 and introduced via a line 15 into an oil-water separation drum 16. After the oil-water separation, the dimerized aldehyde is separated and recovered from a line 17. An aqueous layer containing the basic catalyst, separated by the oil-water separation drum 16, will be recycled via lines 18, 20 and 21 to the reactive distillation column 3.

On the other hand, from the bottom of the reactive distillation column 3, an aqueous basic catalyst solution and high boiling point compounds are withdrawn from a line 9 and subjected to oil-water separation by an oil-water separation drum 10. Then, an aqueous layer containing the basic catalyst is recycled via a line 21 to the reactive distillation column 3. An organic layer containing high boiling point compounds, separated by the oil-water separation drum 10, is discharged via a line 11 and will effectively be used, for example, as a fuel.

Further, water formed by the dehydration reaction constitutes an azeotrope together with the dimerized aldehyde and the feed aldehyde contained in a small amount. The azeotrope is withdrawn in a vapor state from a line 22 and cooled by a condenser 23 and introduced via a line 24 into an oil-water separation drum 25. By the oil-water separation, the formed water, and an organic layer containing the feed aldehyde and the dimerized aldehyde, are separated. The separated formed water is discharged via a line 27. Further, the dimerized aldehyde and the feed aldehyde contained in a small amount are recovered from a line 26.

The reactive distillation column to be used in the present invention is not particularly limited, so long as gas-liquid equilibrium can substantially be maintained in the column. With a view to suppressing formation of high boiling point compounds, it is preferred to employ a column which has theoretical plates of from 2 to 50 plates in the reaction zone i.e. the contact zone of the aldehyde with the catalyst solution. In the present invention, the reaction zone means section B and section C when the apparatus as shown in FIG. 1, is used. If the number of theoretical plate in the above reaction zone is less than 2 plates, the amount of formed high boiling point compounds tends to increase, whereby the yield of the dimerized aldehyde will decrease. On the other hand, if the number of theoretical plate exceeds 50 plates, the installation cost increases unnecessarily.

The reactive distillation column may be a plate distillation column or a packed distillation column. The structure of plates in the plate distillation column is not particularly limited, and it may be any structure so long as the feed aldehyde and the basic catalyst liquid can be intimately contacted on the plates. For example, cross stream contact type trays or counter-current contact type trays, such as bubble cap trays, perforated trays or bubble trays, may be used. Likewise, the packed distillation column is not particularly limited, and a regular packing material or an irregular packing material may be employed.

Further, the manner of introducing the feed aldehyde and the basic catalyst liquid into the reactive distillation column may be optionally selected i.e. may be counter-current or cocurrent. The operational pressure of the reactive distillation column is usually optionally selected within a range of from atmospheric pressure to 10 kg/cm². The operation may be conducted under reduced pressure without any particular problem. However, when the boiling point of the feed aldehyde is low, a special cooling means may sometimes be required at the top of the reactive distillation column.

The temperature in the reactive distillation column may optionally be set by the pressure in the column. For example, when the aldehyde is NBD, the operation may be carried out within a range of from 70° to 110° C. under atmospheric pressure.

According to the method of the present invention, it is possible to utilize the heat of reaction of the condensation and the dehydration reaction as a part of the heat energy required for the distillation operation, which is economically advantageous.

Now, the present invention will be described in further detail with reference to Examples. However, it should be

9 understood that the present invention is by no means restricted by such specific Examples.

EXAMPLE 1

A condensation and a dehydration reaction of NBD obtained by a hydroformylation reaction of propylene, was carried out by means of an apparatus as shown in FIG. 1.

The reactive distillation column 3 is a column having an inner diameter of 35 mm and provided with section A (NBD recovery zone) with theoretical plates of 2 plates, section B (reaction zone) with theoretical plates of 20 plates and section C (reaction zone) with theoretical plates of 2 plates, and as the basic catalyst, a 2% sodium hydroxide aqueous solution was used. Feed NBD and the basic catalyst were supplied at flow rate of 50 ml/hr from lines 1 and 2, respectively, and the reaction was carried out under atmospheric pressure. The NBD content in the organic feed stream supplied from the line 1 was at least 99 wt %. Heating was carried out by a reboiler 8 disposed at the lowest section of the reactive distillation column 3, and the feed aldehyde in a gas-liquid mixed state was contacted with the basic catalyst in a liquid state in the column, so that a substantially steady state of gas-liquid equilibrium was maintained. In the steady state, the temperature in the column was 68° C. at the top and 103° C. at the bottom. Formed EPA was withdrawn together with water in a vapor state from a line 13, cooled by a condenser 14 and then supplied to an oil-water separation drum 16. An oil layer containing formed EPA was withdrawn from a line 17 and analyzed by gas chromatography. On the other hand, water separated by the oil-water separation drum 16 was withdrawn from a line 18, and water corresponding to the amount formed by the reaction was purged by a line 19, and the rest was recycled via lines 20 and 21 to the reactive distillation column 3.

The basic catalyst liquid and high boiling point compounds formed in a very small amount, were sent to an oil-water separation drum 10 by a line 9 at the bottom of the reactive distillation column 3, whereupon the high boiling compounds were discharged from a line 11 and analyzed by gas chromatography. On the other hand, the basic catalyst liquid was withdrawn from a line 21, combined with water from the line 20 and recycled for reuse to the reactive distillation column 3 via the line 21. Upon initiation of this recycling, supply of the basic catalyst liquid from the line 2 was stopped.

The vapor distilled from the top of the column was cooled and condensed by a condenser, and the liquefied stream was sent to a reflux drum 7. This liquefied stream contained at least about 95% of NBD. Further, a predetermined amount of reflux was carried out by a line 4, and the amount of the liquid withdrawn from a line 5 was adjusted to maintain the liquid surface of the reflux drum 7 to be constant. The results obtained by this series of operations, are shown in Table 1.

EXAMPLE 2

The operations were carried out in the same manner as in Example 1 except that the number of theoretical plate of section B of the reactive distillation column 3 was changed to 8 plates. The results are shown in Table 1.

EXAMPLE 3

The operations were carried out in the same manner as in Example 1 except that the number of theoretical plate of section B of the reactive distillation column 3 was changed to 4 plates. The results are shown in Table 1.

EXAMPLE 4

The operations were carried out in the same manner as in Example 1 except that the number of theoretical plate of section B of the reactive distillation column 3 was changed to 2 plates. The results are shown in Table 1.

EXAMPLE 5

The operations were carried out in the same manner as in Example 1 except that the number of theoretical plate of section B of the reactive distillation column 3 was changed to 1 plate. The results are shown in Table 1.

EXAMPLE 6

The operations were carried out in the same manner as in Example 1 except that in the apparatus as shown in FIG. 1, the feeding position of NBD was changed to the lowest position of section B, and plates corresponding to 3 theoretical plates were provided between this feeding position and section C. The results are shown in Table 1.

COMPARATIVE EXAMPLE 1

A condensation and a dehydration reaction was carried out by two stirring tank reactors connected in series. Using a 2% NaOH aqueous solution as the basic catalyst, the reaction was carried out by supplying NBD and the basic catalyst liquid at a flow rate of 50 ml/hr, respectively, under atmospheric pressure at a reaction temperature of 90° C. for a residence time of 15 minutes per each reactor. The results are shown in Table 1.

TABLE 1

| | The number of theoretical plates of reaction zones | Conversion of NBD (%) | Yield of EPA (%) | Yield of high boiling point substances (%) |
|---|---|---|---|---|
| Example 1 | 22 | 99.9 | 99.6 | 0.3 |
| Example 2 | 10 | 99.7 | 99.3 | 0.4 |
| Example 3 | 6 | 99.3 | 99.0 | 0.3 |
| Example 4 | 4 | 98.9 | 98.4 | 0.5 |
| Example 5 | 3 | 98.0 | 97.0 | 1.0 |
| Example 6 | 25 | 99.9 | 99.6 | 0.3 |
| Comparative Example 1 | — | 99.2 | 97.0 | 2.2 |

EXAMPLE 7

A condensation and a dehydration reaction of NBD obtained by a hydroformylation reaction of propylene, was carried out by means of an apparatus having a construction as shown in FIG. 2.

The reactive distillation column 3 was a column having an internal diameter of 75 mm and provided with section A (NBD recovery zone) with theoretical plates of 5 plates, section B (reaction zone) with theoretical plates of 20 plates and section C (reaction zone) with theoretical plates of 5 plates, and as the basic catalyst, a 2% sodium hydroxide aqueous solution was used. Feed NBD and the basic catalyst were supplied at a flow rate of 75 ml/hr and 225 ml/hr from lines 1 and 2, respectively, and the reaction was carried out under atmospheric pressure. The NBD content in the organic feed stream supplied from the line 1 was at least 99 wt %. Heating was carried out by a reboiler 8 disposed at the lowest position of the reactive distillation column 3, and the feed aldehyde in a gas-liquid mixed state was contacted with the basic catalyst liquid in a liquid state in the column, so that a substantially steady state of gas-liquid equilibrium was maintained in the column. In the steady state, the temperature in the column was 68° C. at the top and 103° C. at the bottom.

Formed EPA was withdrawn in a liquid state together with the aqueous sodium hydroxide solution from a line 13, cooled by a condenser 14 and then supplied to an oil-water separation drum 16 by a line 15. The oil layer containing EPA as the product, was withdrawn from a line 17 and analyzed by gas chromatography. On the other hand, the aqueous layer separated by the oil-water separation drum 16 was withdrawn from a line 18 and recycled to the reactive distillation column 3 via lines 20 and 21.

Further, an azeotrope of water and an oil content was withdrawn in a vapor state from a line 22, cooled by a condenser 23 and introduced to an oil-water separation drum 25 by a line 24. Here, formed water and an oil layer containing EPA were separated by oil-water separation. The separated formed water is discharged via a line 27. The discharged flow rate was 8 ml/hr. A part of the discharged formed water was sampled, and the oil content in the water was analyzed by gas chromatography. On the other hand, the separated oil layer containing EPA was withdrawn from a line 26 and analyzed by gas chromatography.

The position of the line 22 at that time was a position corresponding to the 20th plate in the theoretical plates downward from the feeding position of the feed aldehyde and the aqueous basic catalyst solution.

The aqueous basic catalyst solution and high boiling point compounds formed in a very small amount were sent to an oil-water separation drum 10 by a line 9 at the bottom of the reactive distillation column 3, and the high boiling point compounds were discharged from a line 11 and analyzed by gas chromatography. On the other hand, the aqueous solution containing the basic catalyst was withdrawn from a line 21 and combined with the aqueous solution from the line 20. The combined aqueous solution was recycled to the reactive distillation column 3 via a line 21. Upon initiation of this recycling, supply of the aqueous basic catalyst solution from the line 2 was stopped.

Further, the vapor distilled from the top of the column was cooled and condensed by a condenser 6, and the condensed stream was sent to a reflux drum 7. The liquefied stream contained at least about 95% of NBD. Further, a predetermined amount of reflux was carried out to the top of the column by a line 4. The amount of the liquid withdrawn from a line 5 was adjusted so that the liquid surface of the reflux drum 7 was maintained at a constant level. The results obtained by this series of operations are shown in Table 2.

EXAMPLE 8

The operations were carried out in the same manner as in Example 7 except that the position of the line 22 was a position corresponding to the 10th plate in the theoretical plates downward from the feeding position of the feed aldehyde and the aqueous basic catalyst solution. The results are shown in Table 2.

EXAMPLE 9

The operations were carried out in the same manner as in Example 7 except that the position of the line 22 was a position corresponding to the 8th plate in the theoretical plates downward from the feeding position of the feed aldehyde and the aqueous basic catalyst solution. The results are shown in Table 2.

EXAMPLE 10

The operations were carried out in the same manner as in Example 7 except that the position of the line 22 was at the top of the tower. The results are shown in Table 2.

COMPARATIVE EXAMPLE 2

The operations were carried out in the same manner as in Example 7 except that withdrawal from the line 22 was terminated, and the amount of water corresponding to the water formed by the dehydration reaction, was purged from the line 19. The results are shown in Table 2.

TABLE 2

| | The vapor composition in the column at the position of line 22 (DA/UA value) | Loss of NBD from line 27[1] (%) | Concentration of water-polluting substances[2] in line 27 (wt %) |
|---|---|---|---|
| Example 7 | 499 | 0.001 | 0.1 or less |
| Example 8 | 10.5 | 0.01 | 0.1 or less |
| Example 9 | 1.36 | 0.3 | 0.1 or less |
| Example 10 | 0.1 or less | 0.6 | 0.1 or less |
| Comparative Example 2 | — | 0.001[3] | 3.0 or more[4] |

[1]Loss of NBD (%) = PNBD/FNBD
PNBD: The amount of NBD purged from line 27 (g/h)
FNBD: The amount of NBD fed from line 1 (g/h)
[2]Water-polluting substances: NaOH, butyric acid and sodium butyrate
[3]Loss of NBD from line 19.
[4]Concentration of water-polluting substances in line 19.

By subjecting an aldehyde to a condensation and a dehydration reaction in accordance with the method of the present invention, it is possible to suppress formation of high boiling point compounds to a minimum level even without adding a reaction terminator or the like in order to improve the selectivity for a dimerized aldehyde, and it is thereby possible to produce the dimerized aldehyde highly selectively. Further, according to the method of the present invention, the catalyst solution can be reused by recycling, and thus the method is advantageous particularly when it is carried out continuously. By using a reactive distillation column, the condensation reaction and the dehydration reaction can be carried out simultaneously, whereby it is possible to remarkably reduce the installation cost when the method is to be practically used for an industrial operation.

Further, according to the method of the present invention, the reaction heat of the condensation dehydration reaction can be utilized as a part of the heat energy required for the distillation operation, and such is economically advantageous. Besides, the loss of the feed aldehyde can be minimized to such an extent that it is satisfactory for an industrial operation, and the water formed by the dehydration reaction can be separated without requiring a complicated step which is economically disadvantageous. Further, the amount of water-polluting substances discharged from the process can be minimized, whereby no extra installation for waste water treatment will be required, whereby the installation cost for the industrial application can remarkably be reduced.

What is claimed is:

1. A method for producing a dimerized aldehyde, which comprises subjecting a feed aldehyde to a condensation reaction and a dehydration reaction in the presence of a basic catalyst, wherein the feed aldehyde is the one having one or two hydrogen atoms at the α-position, an organic feed stream containing the feed aldehyde is supplied to a reactive distillation column, and the condensation reaction and the dehydration reaction are carried out simultaneously in the reactive distillation column.

2. The method for producing a dimerized aldehyde according to claim 1, wherein at least 50 wt % of the organic feed stream containing the feed aldehyde is the aldehyde having two hydrogen atoms at the α-position.

3. The method for producing a dimerized aldehyde according to claim 2, wherein at least 70 wt % of the organic feed stream containing the feed aldehyde is the aldehyde having two hydrogen atoms at the α-position.

4. The method for producing a dimerized aldehyde according to claim 1, wherein water formed by the dehydration reaction is withdrawn in a vapor state from the reactive distillation column.

5. The method for producing a dimerized aldehyde according to claim 4, wherein the formed water is withdrawn from a position where the weight ratio of the dimerized aldehyde to the feed aldehyde in the vapor composition in the reactive distillation column, is at least 0.5.

6. The method for producing a dimerized aldehyde according to claim 5, wherein the formed water is withdrawn from a position where the weight ratio of the dimerized aldehyde to the feed aldehyde in the vapor composition in the reactive distillation column, is at least 0.8.

7. The method for producing a dimerized aldehyde according to claim 1, wherein water formed by the dehydration reaction is discharged by flushing a part of a basic catalyst liquid stream or a part of a mixed liquid stream of the basic catalyst liquid and the reaction product, withdrawn from the reactive distillation column.

8. The method for producing a dimerized aldehyde according to claim 7, wherein the position from which the basic catalyst liquid stream or the mixed liquid stream is withdrawn from the reactive distillation column, is a position where the weight ratio of the dimerized aldehyde to the feed aldehyde in the liquid composition, is at least 0.5.

9. The method for producing a dimerized aldehyde according to claim 8, wherein the position from which the basic catalyst liquid stream or the mixed liquid stream is withdrawn from the reactive distillation column, is a position where the weight ratio of the dimerized aldehyde to the feed aldehyde in the liquid composition is at least 0.8.

10. The method for producing a dimerized aldehyde according to claim 1, wherein contact of the feed aldehyde with the basic catalyst in the reactive distillation column is carried out in such a manner that the feed aldehyde in a gas-liquid mixed state is intimately contacted with the basic catalyst liquid in a liquid state.

11. The method for producing a dimerized aldehyde according to claim 1, wherein the feed aldehyde consists of n-butyraldehyde, isobutyraldehyde or a mixture thereof.

12. The method for producing a dimerized aldehyde according to claim 1, wherein the feed aldehyde consists of valeraldehyde, 2-methylbutyraldehyde or a mixture thereof.

13. The method for producing a dimerized aldehyde according to claim 1, wherein the basic catalyst is a catalyst comprising a water-soluble inorganic basic compound.

14. The method for producing a dimerized aldehyde according to claim 13, wherein the basic catalyst is a catalyst comprising a basic compound of an alkali metal or an alkaline earth metal.

15. The method for producing a dimerized aldehyde according to claim 14, wherein the basic catalyst is a catalyst comprising a hydroxide of an alkali metal.

16. The method for producing a dimerized aldehyde according to claim 15, wherein the basic catalyst is a catalyst comprising sodium hydroxide, potassium hydroxide, lithium hydroxide or a mixture thereof.

17. The method for producing a dimerized aldehyde according to claim 13, wherein the basic catalyst is used in the form of an aqueous solution.

18. The method for producing a dimerized aldehyde according to claim 1, wherein the reactive distillation column is a plate distillation column having plates provided in the column and having theoretical plates of from 2 to 50 plates in the reaction zone.

19. The method for producing a dimerized aldehyde according to claim 1, wherein the reactive distillation column is a packed distillation column having a packing material provided in the column and having theoretical plates of from 2 to 50 plates in the reaction zone.

20. A method for producing a dimerized aldehyde, which comprises subjecting a feed aldehyde to a condensation reaction and a dehydration reaction in the presence of a basic catalyst, wherein an organic feed stream containing the feed aldehyde is supplied to a reactor, and the condensation reaction and the dehydration reaction are carried out simultaneously in the reactor, wherein contact of the feed aldehyde with the basic catalyst in the reactor is carried out in such a manner that the feed aldehyde in a gas-liquid mixed state is intimately contacted with the basic catalyst liquid in a liquid state.

21. The method for producing a dimerized aldehyde according to claim 20, wherein the reactor is a reactive distillation column.

22. The method for producing a dimerized aldehyde according to claim 20, wherein at least 50 wt % of the organic feed stream containing the feed aldehyde is the aldehyde having two hydrogen atoms at the α-position.

23. The method for producing a dimerized aldehyde according to claim 20, wherein contact of the feed aldehyde with the basic catalyst liquid, is carried out under a pressure of from 0.4 to 12.0 $kg/cm^2$ at a temperature of from 50° to 180° C.

24. A method for producing a dimerized aldehyde, wherein a distillation column is used which has a feed inlet at an intermediate section of the column and which is provided with liquid phase-maintaining means located in the column above and below the feed inlet, wherein an alkali catalyst is present on the liquid phase-maintaining means located below the feed inlet, a feed aldehyde containing an aldehyde having two hydrogen atoms at the α-position, is supplied from the feed inlet, a condensation reaction and a dehydration reaction of the feed aldehyde are carried out in the column to form a dimerized aldehyde having an unsaturated bond, a low boiling point fraction containing the feed aldehyde and water is distilled from above the feed inlet of the distillation column, while a formed mixture containing the dimerized aldehyde is withdrawn from below the feed inlet of the distillation column, and the dimerized aldehyde is recovered from the formed mixture.

25. The method for producing a dimerized aldehyde according to claim 24, wherein the formed mixture containing the dimerized aldehyde is withdrawn from an intermediate position between the feed inlet and the bottom of the distillation column.

26. The method for producing a dimerized aldehyde according to claim 24, wherein at least a part of the liquid phase-maintaining means comprises plates.

27. The method for producing a dimerized aldehyde according to claim 24, wherein at least a part of the liquid phase-maintaining means comprises a packing material.

28. The method for producing a dimerized aldehyde according to claim 24, wherein the liquid phase-maintaining means located below the feed inlet has theoretical plates of from 2 to 50 plates.

29. The method for producing a dimerized aldehyde according to claim 24, wherein the distillation column is a distillation column provided with a reboiler, and the liquid stream supplied to the reboiler, is a liquid stream wherein the weight ratio of an organic phase containing the dimerized aldehyde as the main component to an aqueous phase containing the basic catalyst, is at most 0.1.

* * * * *